(12) United States Patent
Lucas et al.

(10) Patent No.: US 12,247,907 B2
(45) Date of Patent: *Mar. 11, 2025

(54) AUTOMATED AIRBORNE PARTICULATE MATTER COLLECTION, IMAGING, IDENTIFICATION, AND ANALYSIS

(71) Applicant: Pollen Sense LLC, Provo, UT (US)

(72) Inventors: Richard Lucas, Phoenix, AZ (US); Landon Bunderson, Castle Dale, UT (US); Nathan Allan, Mapleton, UT (US); Kevn Lambson, Lewis, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 18/297,997

(22) Filed: Apr. 10, 2023

(65) Prior Publication Data

US 2023/0358661 A1 Nov. 9, 2023

Related U.S. Application Data

(63) Continuation of application No. 17/592,374, filed on Feb. 3, 2022, now Pat. No. 11,624,695, which is a
(Continued)

(51) Int. Cl.
*G01N 15/06* (2024.01)
*B03C 3/36* (2006.01)
(Continued)

(52) U.S. Cl.
CPC ............ *G01N 15/0227* (2013.01); *B03C 3/36* (2013.01); *B03C 3/45* (2013.01); *G01N 1/2202* (2013.01);
(Continued)

(58) Field of Classification Search
CPC ............. G01N 15/0227; G01N 1/2202; G01N 1/2273; G01N 1/40; G01N 15/0612;
(Continued)

(56) References Cited

U.S. PATENT DOCUMENTS

| 4,693,733 A | 9/1987 | Fuzimura |
| 10,724,935 B2 | 9/2020 | Lucas et al. |

(Continued)

FOREIGN PATENT DOCUMENTS

| CN | 203299089 U | 11/2013 |
| WO | WO 2009035483 A2 | 3/2009 |

(Continued)

OTHER PUBLICATIONS

English translation of CN203299089 pepaired by Google Patents (https://patents.google.com/patent/CN203299089U/en?oq=CN+203299089).

*Primary Examiner* — John R Schnurr
(74) *Attorney, Agent, or Firm* — Intellectual Strategies (57) ABSTRACT

The following is an apparatus and a method that enables the automated collection and identification of airborne particulate matter comprising dust, pollen grains, mold spores, bacterial cells, and soot from a gaseous medium comprising the ambient air. Once ambient air is inducted into the apparatus, aerosol particulates are acquired and imaged under a novel lighting environment that is used to highlight diagnostic features of the acquired airborne particulate matter. Identity determinations of acquired airborne particulate matter are made based on captured images. Abundance quantifications can be made using identity classifications. Raw and summary information are communicated across a data network for review or further analysis by a user. Other than routine maintenance or subsequent analyses, the basic operations of the apparatus may use, but do not require the active participation of a human operator.

4 Claims, 6 Drawing Sheets

Related U.S. Application Data continuation of application No. 16/909,380, filed on Jun. 23, 2020, now Pat. No. 11,275,011, which is a continuation of application No. 15/525,069, filed as application No. PCT/US2015/059278 on Nov. 5, 2015, now Pat. No. 10,724,935.

(60) Provisional application No. 62/076,507, filed on Nov. 7, 2014.

(51) Int. Cl.

| | |
|---|---|
| *B03C 3/45* | (2006.01) |
| *G01N 1/22* | (2006.01) |
| *G01N 1/40* | (2006.01) |
| *G01N 15/0227* | (2024.01) |
| *G01N 15/1433* | (2024.01) |
| *G01N 33/00* | (2006.01) |
| *G06F 18/24* | (2023.01) |
| *G06T 7/11* | (2017.01) |
| *H04N 23/56* | (2023.01) |
| *H04N 23/67* | (2023.01) |
| *H04N 23/74* | (2023.01) |
| *G01N 15/00* | (2006.01) |
| *G01N 15/01* | (2024.01) |
| *G01N 15/10* | (2006.01) |
| *G01N 15/14* | (2006.01) |
| *G06T 7/60* | (2017.01) |
| *G06T 7/73* | (2017.01) |
| *H04N 5/33* | (2023.01) |

(52) U.S. Cl.
CPC ............. *G01N 1/2273* (2013.01); *G01N 1/40* (2013.01); *G01N 15/0612* (2013.01); *G01N 15/0637* (2013.01); *G01N 15/1433* (2024.01); *G01N 33/0004* (2013.01); *G01N 33/0062* (2013.01); *G06F 18/24* (2023.01); *G06T 7/11* (2017.01); *H04N 23/56* (2023.01); *H04N 23/67* (2023.01); *H04N 23/74* (2023.01); *G01N 2001/2223* (2013.01); *G01N 2001/2291* (2013.01); *G01N 2001/4038* (2013.01); *G01N 2015/0046* (2013.01); *G01N 15/01* (2024.01); *G01N 2015/1006* (2013.01); *G01N 2015/1493* (2013.01); *G01N 33/0068* (2024.05); *G06T 7/60* (2013.01); *G06T 7/73* (2017.01); *G06T 2207/10152* (2013.01); *H04N 5/33* (2013.01)

(58) Field of Classification Search
CPC ........... G01N 15/0637; G01N 15/1475; G01N 33/0004; G01N 33/0062; G01N 2001/2223; G01N 2001/2291; G01N 2001/4038; G01N 2015/0046; G01N 2015/0065; G01N 2015/1006; G01N 2015/1493; G01N 2033/0068; B03C 3/36; B03C 3/45; G06K 9/6267; G06T 7/11; G06T 7/60; G06T 7/73; G06T 2207/10152; H04N 5/2256; H04N 5/23212; H04N 5/2354; H04N 5/33
See application file for complete search history.

(56) References Cited

U.S. PATENT DOCUMENTS

| | | | |
|---|---|---|---|
| 11,275,011 | B2 | 3/2022 | Lucas et al. |
| 11,624,695 | B2* | 4/2023 | Lucas ................. B03C 3/36 |
| | | | 348/164 |
| 2003/0218688 | A1 | 11/2003 | Shaw et al. |
| 2004/0179322 | A1 | 9/2004 | Pletcher et al. |
| 2007/0097366 | A1 | 5/2007 | LeBoeuf et al. |
| 2007/0295208 | A1 | 12/2007 | Fairchild |
| 2007/0295210 | A1 | 12/2007 | Thomas et al. |
| 2008/0304752 | A1 | 12/2008 | Matteoni et al. |
| 2010/0075317 | A1 | 3/2010 | Schneider et al. |
| 2010/0165341 | A1 | 9/2010 | Babico et al. |
| 2013/0059319 | A1 | 3/2013 | Ereldinger et al. |
| 2016/0044217 | A1 | 2/2016 | Richardson et al. |
| 2016/0270656 | A1* | 9/2016 | Samec ................. A61B 3/1015 |

FOREIGN PATENT DOCUMENTS

| | | |
|---|---|---|
| WO | WO 2009035483 A3 | 6/2009 |
| WO | WO 2009108795 A1 | 9/2009 |
| WO | WO 2016073745 A2 | 5/2016 |

* cited by examiner

AUTOMATED AIRBORNE PARTICULATE MATTER COLLECTION, IMAGING, IDENTIFICATION, AND ANALYSIS

TECHNICAL FIELD

The technical field to which the subject matter of this disclosure relates is Environmental Technology.

BACKGROUND (Note: This application references a number of different non-patent publications as indicated throughout the specification by one or more reference numbers within braces, e.g., {x}. A list of these different publications ordered according to these reference numbers can be found below in the section titled "References". Each of these publications is incorporated by reference herein.)

The concentrations of aerosol particulate matter in the ambient air is a top concern to humankind because airborne particulates have been strongly tied to human health consequences by numerous epidemiological studies. Airborne particulates aggravate respiratory illness which is the single largest cause of hospital admissions among children in the United States {1} and is responsible for a cost upwards of $56 billion in terms of health care expenses, lost productivity, and decreased quality of life in the United States {2}. Short-term exposures (hours to several days) to elevated airborne particulate matter have been observed to exacerbate allergies and asthma {3-5}. Longer term exposures (years to decades) to elevated airborne particulate matter have substantially greater health risks such as increasing the probability of heart disease, diabetes, and other chronic disease {6, 7}. Given that the allergenic virulence of some airborne particulates has increased over the past three decades {8}, the prevalence of allergies and asthma in the developed world has greatly increased over the same period {4-6, 9}, and that the expression of asthma and allergies is forecasted to continue to intensify {10-12}, it is important to develop effective mitigation strategies that will temper both the economic and health burdens caused by airborne particulate-triggered respiratory illness. Knowing the types of particulates, their concentrations, and their distribution within a local environment helps in diagnosis, avoidance, and effective treatment.

Additionally, airborne particulate matter is of horticultural, ecological, and biological interest as it has applications in the propagation and health of plants as well as the expansion of scientific knowledge.

Air-quality sampling devices exist, but the ability of such devices to discern characteristics of airborne particulate matter beyond size range and reflectivity is limited. Such devices are useful for determining the quantity of certain sizes of airborne particulate matter, but give little insight into the shape, color, or other physical or biological properties of the airborne particulate matter, and thus are not practical for discerning detail or identifying airborne particulate matter.

Given the differing effects various components of airborne particulate matter on human health and plant well-being, it is important to be able to quickly and reliably characterize the constitution of airborne particulate matter. What is needed is a system and method that automates the collection of the air sample and captures diagnostic images which can then be used to characterize the identity of airborne particulate matter.

DISCLOSURE

The disclosure described herein collects, images, releases, analyzes, and identifies airborne particulate matter suspended in a gaseous medium. The subject matter of the disclosure can function with or without human intervention, can discriminate between different types of airborne particulate matter, and is more efficient and consistent than current methods due to the implementation of a novel collection apparatus and analysis method.

BRIEF DESCRIPTION OF THE DRAWINGS (Note: This disclosure references components within each figure described below. The naming convention used throughout the specification is first to list the figure number, followed by a decimal point, followed by the specific component number of the given figure, prefaced by the word "Figure" or "Figures", as the situation demands, and all included within parentheses, e.g., (x). For example, a reference to the illustration of the induction unit would be made as follows: (FIG. 1.2).)

The features and advantages of the disclosure will become clearer with the following detailed description in connection with the accompanying drawings, wherein:

FIG. 1 is a front-view illustration depicting an embodiment of a portion of the disclosure, with the following components identified:

1: ambient air
2: induction unit
3: airborne particulate inlet aperture
4: weather-resistant enclosure de-emphasized and indicated by a dashed line
5: air chamber
6: electrode (may be the anode)
7: an embodiment of airborne particulate matter 8: deposition surface (or medium of deposition) 9: translation or rotation mechanism
10: spacer tube—part of the perception unit
11: high-resolution magnified digital camera—part of the perception unit
12: pixel light ring—part of the perception unit
13: objective lens—part of the perception unit
14: linear focus apparatus—part of the perception unit
15: main controller board and on-board computer with integrated Wi-fi communication capability
16: motor controllers
17: high-voltage electric field generator unit
18: filter
19: power and network cabling
20: sampling disk and with embedded electrode (may be the cathode). This component bears the deposition surface (FIGS. 1.8 and 3.8) and is the medium of deposition
24: environmental sensors
26: screw stepper.

FIG. 2 is an illustration of a front oblique view (some features have been omitted for clarity) depicting an embodiment of the disclosure, with the following components identified:

2: induction unit
3: airborne particulate inlet aperture
5: static charge air chamber and electrode
10: spacer tube
12: pixel light ring with reflective light baffles
13: objective lens
20: sampling disk and with embedded electrode (may be the cathode). This component bears the deposition surface (FIGS. 1.8 and 3.8)
21: cleaning mechanism electrode.

FIG. 6 is a flowchart representing the steps of the analysis method for collecting, observing, and identifying airborne particulate matter dispersed in a gaseous medium with the following components identified:
- 1: collect airborne particulate matter onto the surface of a deposition medium
- 2: use an imaging device directed towards the medium of deposition to assess the locations and sizes of acquired particulates within the field of view, may be accomplished through image segmentation
- 3: determine the optimal focus location for each particulate using a focus assessment function limited to each particulate's segment boundary
- 4: capture one or more images from many different lighting configurations for each particle at the ideal focal location
- 5: store captured images in a local or remote data repository for identity determination or other analysis.

DETAILED DESCRIPTION

Figure 1:
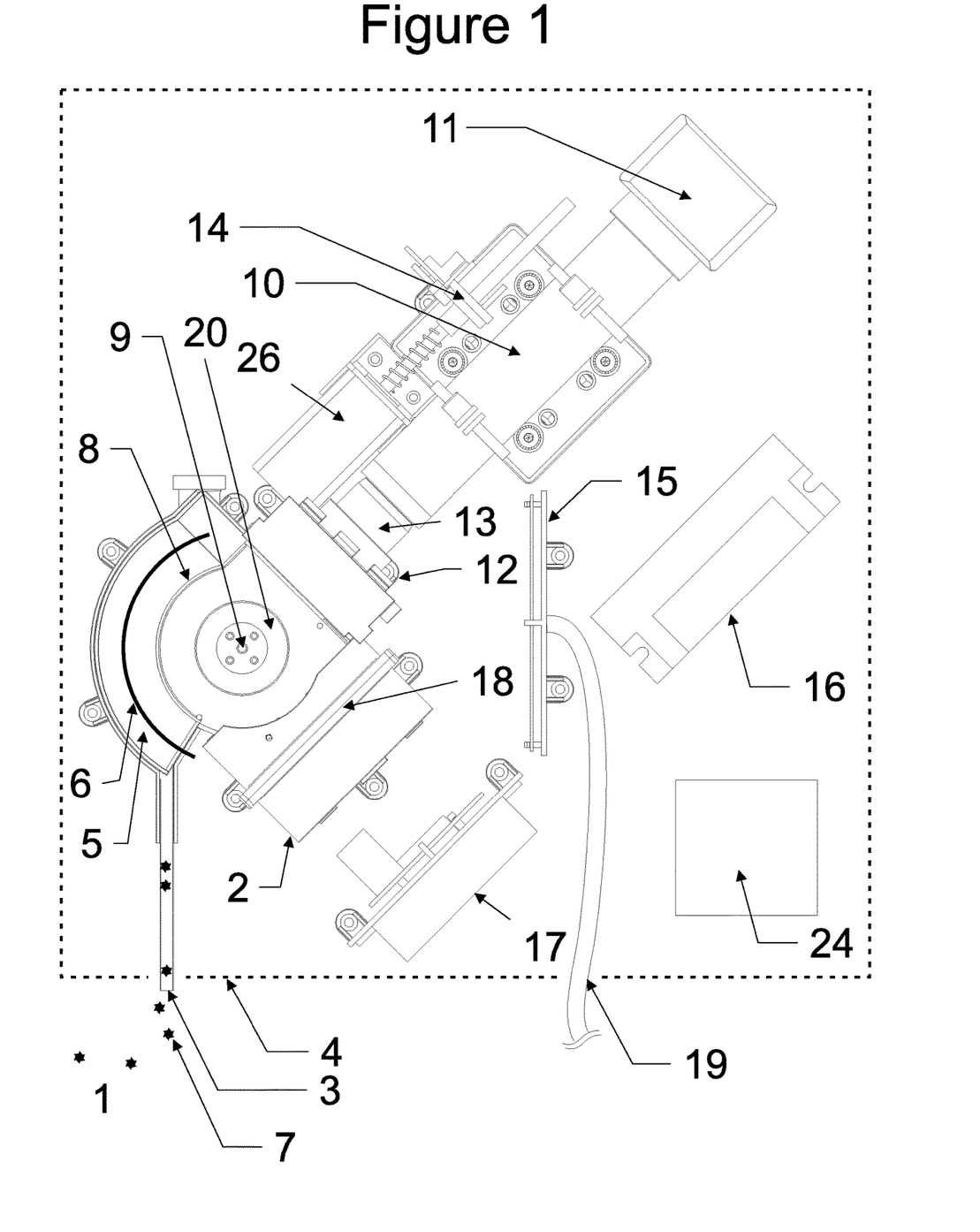
Figure 2:
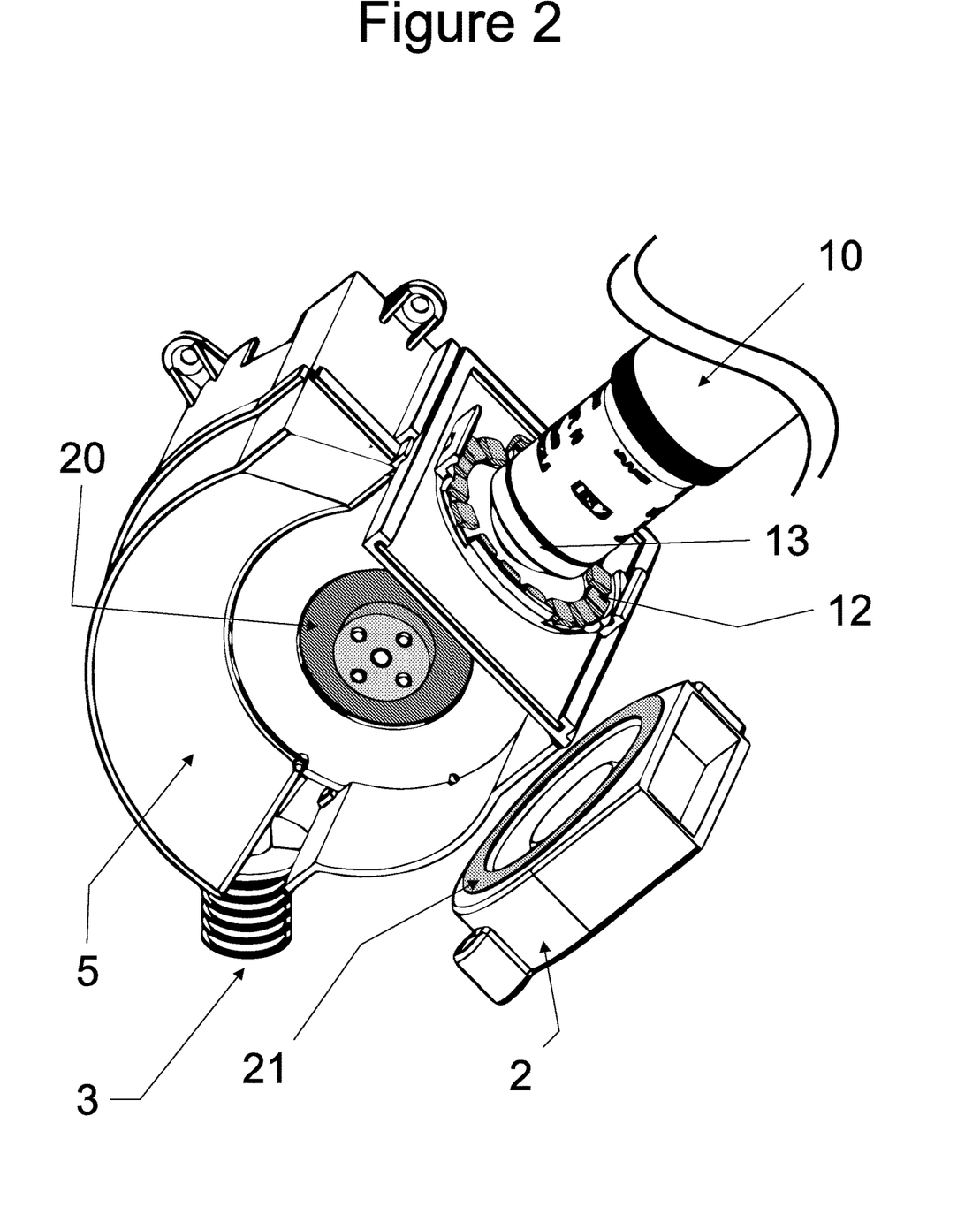

The subject matter of this disclosure represents an automated, computerized, electro-mechanical apparatus (FIG. 1, FIG. 2, FIG. 3, FIG. 4, and FIG. 5) utilizing a combination of hardware and software to acquire, image, identify, quantify, and communicate resulting data describing airborne particulate matter (FIG. 1.7, FIG. 6) dispersed in a gaseous medium (FIG. 1.1). Other than installation, the continued supply of the requisite electrical power (FIG. 1.19), the continuity of a communication network (FIG. 1.19 and FIG. 1.15), and periodic maintenance to the apparatus, the operations of the disclosure described herein can have, but do not require, the presence or actions of a human operator. The typical composition of airborne particulate matter in ambient air is comprised of a complex mixture of dust, pollen grains, fungal spores, bacterial cells, viruses, by-products of internal engine combustion that comprise components of air pollution including hydrocarbons, and other compounds. The resulting data, which are the net product of the apparatus and its associated software, are images, identities, and quantifications of aerosol particulates. Such data may be used for a variety of purposes which include improving the diagnosis and avoidance of airborne particulate matter-related human health issues, plant reproduction, and other air pollution applications.

Figure 6:
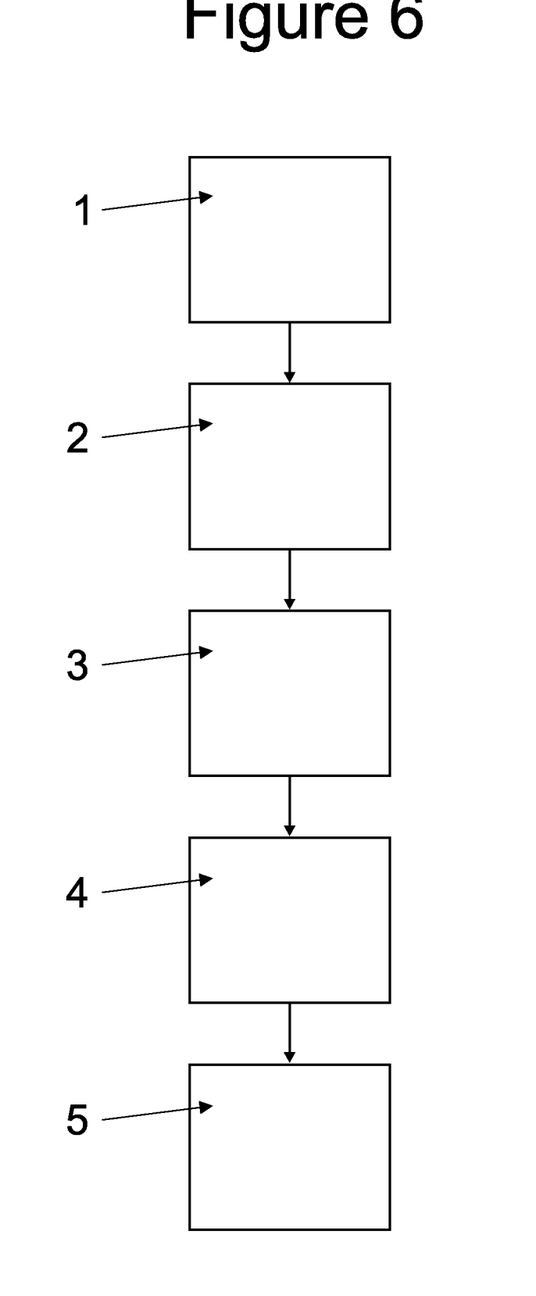

The disclosure is comprised of the following components: a collection system (FIG. 1.2, FIG. 1.3, FIG. 1.5, FIG. 1.6, FIG. 1.8, and FIG. 1.20); a lighting and imaging system (FIG. 1.10, FIG. 1.11, FIG. 1.12, FIG. 1.13, and FIG. 1.14); a release and cleaning system (FIG. 1.2, FIG. 1.18, FIG. 2.21, FIG. 3.18, FIG. 3.22, and FIG. 3.23); and an analysis method (FIG. 6). Each component is described in greater detail below.

Figure 3:
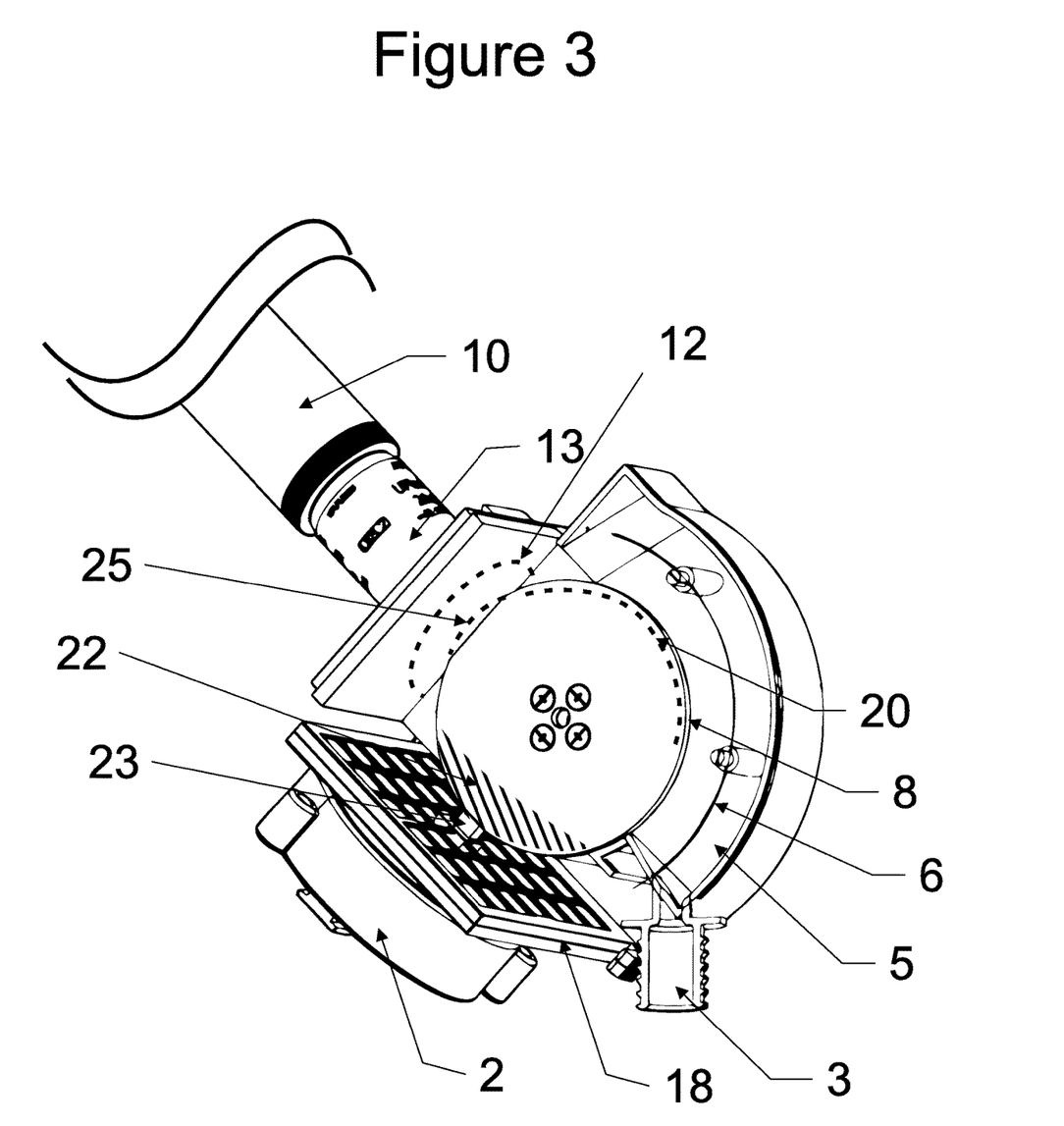
FIG. 3 is an illustration of a back oblique view (some features have been omitted for clarity) depicting an embodiment of the disclosure, with the following components identified:
- 2: induction unit
- 3: airborne particulate inlet aperture
- 5: air chamber
- 6: electrode (may be the anode)
- 8: deposition surface
- 10: spacer tube
- 12: light pixel ring with reflective light baffles
- 13: objective lens
- 18: filter
- 20: sampling disk and with embedded electrodes
- 22: deposition surface cleaning area
- 23: cleaning brush
- 25: imaging area.

The collection system enables the acquisition of airborne particulate matter from the ambient air. An embodiment of this disclosure may utilize an induction unit comprising, but not limited to, a blower fan (FIGS. 1.2, 2.2, 3.2 and 4.2) or other air-flow mechanism to draw ambient air (FIG. 1.1) from the atmosphere into the device through an aperture (FIGS. 1.3, 2.3, 3.3 and 4.3) that may project through an enclosure (FIG. 1.4). The size of the aperture is not important except that it must be known for determining the volume of air flow for calibration and airborne particulate matter quantification purposes. After passing through the aperture (FIGS. 1.3, 2.3, 3.3 and 4.3) and entering the device, the inducted air stream may enter into a larger venturi air chamber (FIGS. 1.5, 2.5, 3.5), and may pass a small electrode (FIGS. 1.6 and 3.6). The electrode may be negatively charged (an anode) and may act to increase the negative charge of passing airborne particulates (FIG. 1.7). A high-voltage electric field generator unit (FIG. 1.17) may create an electrostatic force and may also act to generate an oppositely charged field on a second electrode (a cathode) which may be situated under the deposition surface (FIG. 1.8 and FIG. 3.8). The electrostatic force created between the negatively charged airborne particulate matter and the positive electric field induced on the deposition surface may draw airborne particulates onto the deposition surface (FIG. 1.8 and FIG. 3.8), also referred to as the medium of deposition (FIG. 1.20). Periodically, a motor (FIGS. 1.9 and 4.9) or other translation or rotation mechanism (FIGS. 1.20, 2.20, 3.20 and 4.20) may engage to move the deposition surface such that additional airborne particulate matter may deposit on a different portion of the deposition surface (FIG. 1.8, FIG. 3.8, and FIG. 1.20). An embodiment of the disclosure may utilize a rotating disk with an embedded electrode (FIGS. 2.20, 3.20 and 4.20) that is oppositely charged relative to the airborne particulate matter and which may attract the airborne particulates to the edge of a disk (FIGS. 1.8, 3.8 and 5.3). The deposition surface is continuous, allowing the observation of airborne particulate matter to occur simultaneous with collection or after a delay following collection.

In an embodiment of the disclosure, the collection system may temporarily shut off and discontinue acquisition of airborne particulate matter from the ambient air in the event of inclement weather conditions. Inclement weather may comprise stormy conditions with abnormally high levels of wind that may allow moisture or excessive levels of dust to enter the aperture (FIG. 1.3). Information regarding the local weather or other environmental information used to determine control of the collection system may be retrieved over a communication network via a cable (FIG. 1.19), a Wi-Fi connection integrated with the onboard computer (FIG. 1.15), or from environmental sensors (FIG. 1.24) comprising air pressure, humidity, and temperature, integrated with the main controller board and on-board computer (FIG. 1.15).

Figure 4:
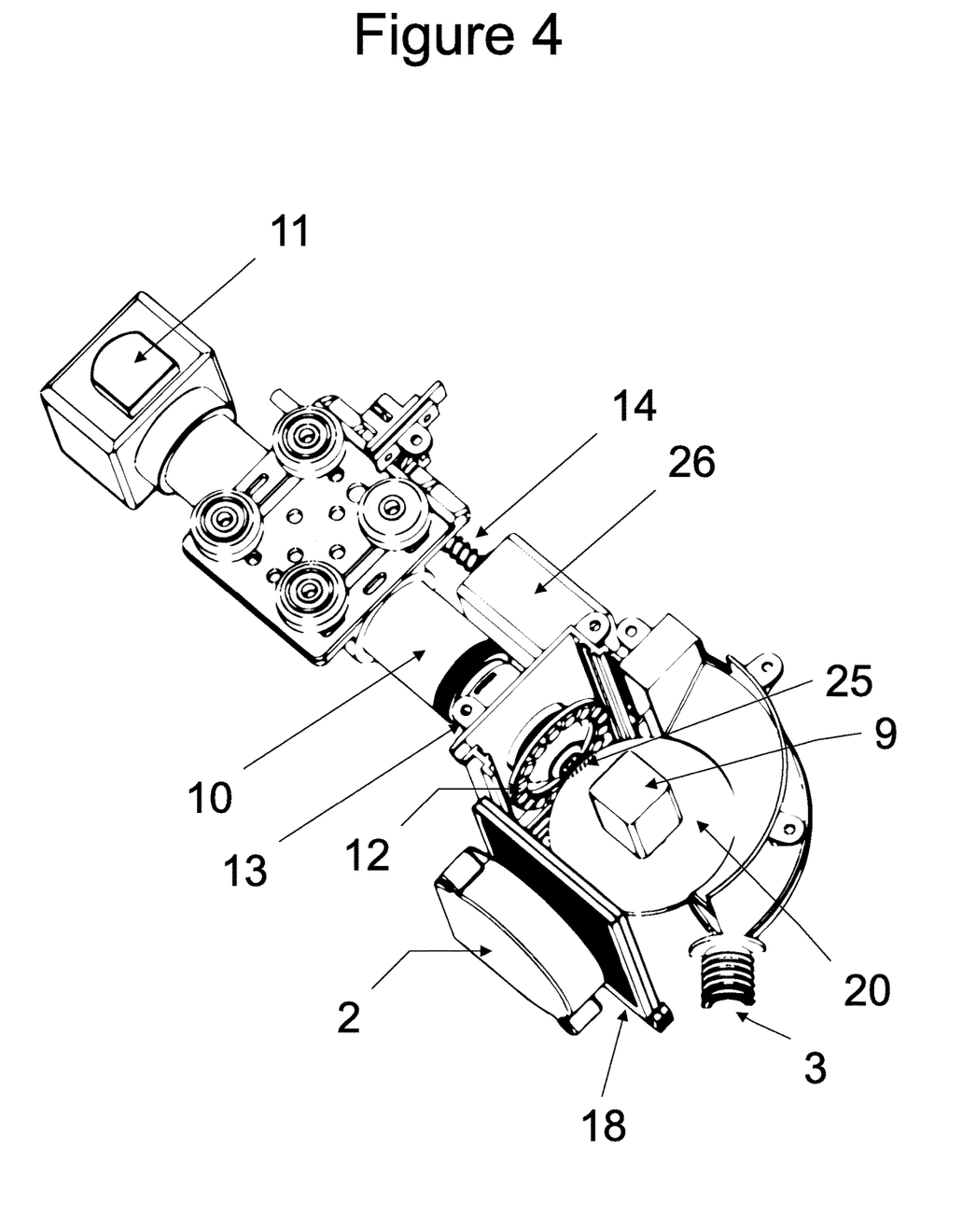
FIG. 4 is an illustration of a rear oblique view (some features have been omitted for clarity) depicting an embodiment of the disclosure, with the following components identified:
- 2: induction unit
- 3: airborne particulate inlet aperture 9: translation or rotation mechanism 10: spacer tube
- 12: light pixel ring with reflective baffles
- 13: objective lens
- 14: focus mechanism comprising a linear rail, a motor and end-stops
- 18: filter
- 20: sampling disk and with embedded electrode (may be the cathode). This component bears the deposition surface (FIGS. 1.8 and 3.8)
- 25: imaging area
- 26: screw stepper.
Figure 5:
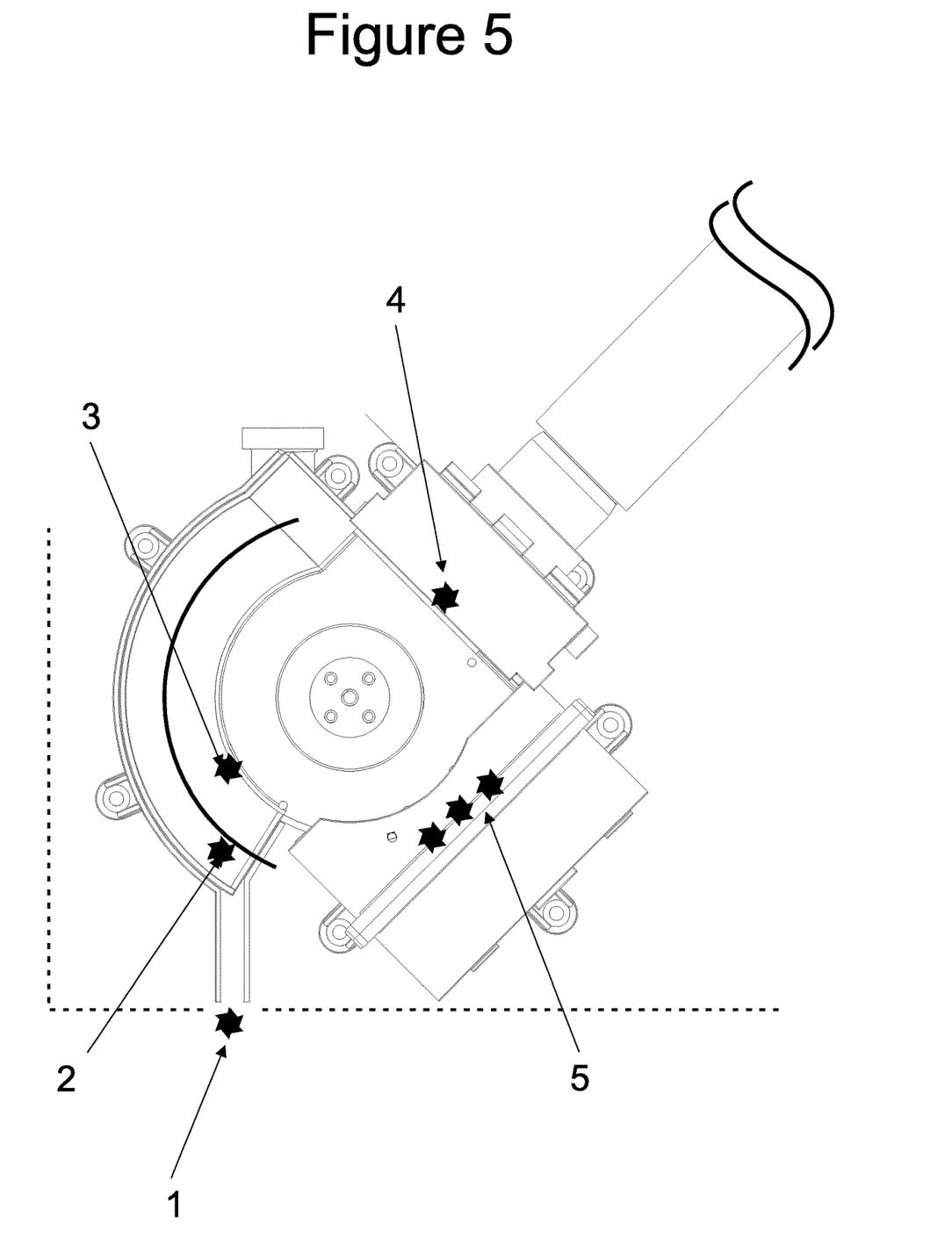
FIG. 5 is an illustration of a front view depicting an embodiment of the disclosure, detailing the flow of particulates through the system with the following components identified:
- 1: an airborne particulate (enlarged and not to scale) enters the airborne particulate inlet aperture
- 2: electrostatic charge imparted to particulate(s)
- 3: particulate(s) deposited on deposition surface
- 4: illumination and imaging of particulate(s)
- 5: brush, airstream, electrostatic charge, gravity, and filter clean deposition surface.

The lighting and imaging system enables the capture, recording, and storage of images of sufficient quality for analyses and identification of the acquired airborne particulate matter. In an embodiment of the disclosure, a motor (FIGS. 1.9 and 4.9) may rotate the deposition surface (FIG. 1.8, FIG. 3.8, and FIG. 1.20) and thus convey the acquired airborne particulate matter from the collection area to the imaging area (FIG. 3.25 and FIG. 4.25). The imaging area (FIG. 3.25 and FIG. 4.25) may be encased in glass to avoid air flow at the imaging location. An embodiment of this disclosure may utilize a finite objective lens (FIG. 1.13), a spacing tube (FIG. 1.10), and a high-resolution magnified camera (FIG. 1.11) or other optical or electronic sensor technology and an associated light/radiation system (FIG. 1.12, FIG. 2.12, and FIG. 3.12) to capture and record digital representations of the acquired airborne particulate matter. The objective lens (FIG. 1.13), spacing tube (FIG. 1.10), a high-resolution magnified camera (FIG. 1.11) or other electronic/optical sensor technology, and associated light/radiation system (FIG. 1.12, FIG. 2.12, and FIG. 3.12) comprise the perception unit for human or machine observation of the airborne particulate matter. Magnification of the perception unit may be accomplished via optical means, digital means or both and may comprise an objective lens or series of lenses (FIG. 1.13), a spacing tube (FIG. 1.10), a high-resolution magnified camera (FIG. 1.11), or other optical or electronic sensor technology. The field of view of the objective lens (FIG. 1.13, FIG. 2.13, FIG. 3.13 and FIG. 4.13) may be recorded with a digital camera (FIG. 1.11 and FIG. 4.11) or other electronic/optical sensor technology that may be oriented so as to examine the deposition surface (FIG. 1.8, FIG. 3.8, and FIG. 1.20) and the acquired airborne particulate matter thereon.

For lighting, an embodiment of this disclosure may use multiple light and radiation sources, individually controlled, and situated in a ring (FIG. 1.12) surrounding the acquired airborne particulate matter on the deposition surface (FIG. 1.8, FIG. 3.8, and FIG. 1.20). The lighting apparatus may utilize red-green-blue (ROB) light emitting diodes (LED) or other electromagnetic radiation sources similarly situated within the pixel light ring (FIG. 1.12) to illuminate the deposition surface (FIG. 1.8, FIG. 3.8, and FIG. 1.20) within the field of view of the objective lens (FIG. 2.13, FIG. 3.13, and FIG. 4.13) with ultraviolet, visible, and/or near infrared electromagnetic light at a high angle of incidence onto the top adaxial surface of the airborne particulate matter. An embodiment of the disclosure may also include reflective light baffles on the pixel light ring (FIG. 3.12 and FIG. 4.12) to increase the amount of diffuse light in addition to direct light incident to the acquired airborne particulate matter on the deposition surface (FIG. 1.8, FIG. 3.8, and FIG. 1.20). A control unit comprised of a software system, which may be integrated with the main controller board (FIG. 1.15), may individually modulate and rotate the LED pixels through a variety of wavelength combinations from 200 to 800 nanometers and lighting perspectives while the software may cause images of the acquired airborne particulate matter to be captured under each lighting combination in order to obtain a series of obliquely lit, dark-field images captured from different adaxial and diffuse illumination directions, over a range of the electromagnetic frequencies, and across a range of illumination intensities. Obliquely lit and dark-field refer to the adaxial orientation of pixel light ring (FIG. 1.12) and the high-resolution magnified digital camera (FIG. 1.11) relative to the acquired airborne particulate matter on the deposition surface (FIG. 1.8, FIG. 3.8, and FIG. 1.20) which is illuminated with light and other electromagnetic radiation both on its top surface and/or diffusely. To reduce camera noise, multiple camera frames may be captured of each perspective and lighting combination, and the frames may be averaged together into a composite image. Knowledge of the direction, frequency, and intensity of the light source may be used to highlight and infer topological features of the acquired airborne particulate matter including pores and furrows of pollen grains and septae or mycelia fragments of spores.

In an embodiment of this disclosure, the imaging system may have a linear focus apparatus (FIG. 1.14) which may allow the software to seek out ideal focus on a particulate-specific basis. The high-resolution magnified digital camera (FIG. 1.11), the spacer tube (FIG. 1.10), the objective lens (FIG. 1.13), or the pixel light ring (FIG. 1.12) may ride on a linear carriage (FIGS. 1.14 and 4.14) to facilitate focusing, which carriage may be translated via a screw stepper (FIG. 1.26 and FIG. 4.26) controlled by a motor controller (FIG. 1.16). Focus may be accomplished in two phases: coarse and fine. Using the digital camera (FIG. 1.11), the computer control system may assess the best focus for the overall field of view (the coarse focus) by incrementally advancing the focus motor (FIG. 4.14) and processing the image through a focus assessment function. Such focus function may consist of bilinear squared difference factored with the overall histogram width. Once the optimal focus location is determined for the overall field of view, image segmentation algorithms (described below) may be used to determine individual particulate locations and sizes. A fine focus process may then be performed whereby the focal point may be translated through a range proximal to the overall optimal. Through this process, the software may take multiple image samples constrained to the boundaries of each segment and at ranged focal positions. The optimal focus position for each segment region may then be determined by taking the best of the focus values for that region. This focus position may then be used as the focus position in the subsequent imaging of each region.

The release and cleaning system enables the evacuation and discharge of the acquired airborne particulate matter from the deposition surface (FIG. 1.8, FIG. 3.8, and FIG. 1.20). Once a portion of the deposition surface (FIG. 1.8, FIG. 3.8, and FIG. 1.20) has been imaged, it may be cleaned before being rotated or translated back into the collection area near the airborne particulate inlet aperture (FIG. 1.3, FIG. 2.3, FIG. 3.3, and FIG. 4.3). Release and cleaning of airborne particulate matter may be accomplished via one or more of the following mechanisms or a combination thereof: reversing the electric charge; airflow; mechanical; physical; gravity; or filter. In an embodiment of the disclosure, the deposition surface (FIG. 1.8, FIG. 3.8, and FIG. 1.20) may be rotated or otherwise translated into a region (FIG. 3.22) where oppositely charged electrodes (FIG. 2.21), a foam or brush cleaning mechanism (FIG. 3.23), passing air being evacuated from the device which may be from the action of the induction unit (FIGS. 1.2, 2.2, 3.2 and 4.2), and gravity may combine to remove the acquired airborne particulate matter and carry it or let it fall passively into a filter (FIGS. 1.18, 3.18, 4.18 and 5.5).

In an embodiment of the disclosure, an electric field may be utilized to repel the acquired airborne particulate matter from the deposition surface (FIG. 1.8, FIG. 3.8, and FIG. 1.20). The creation of an electric field of opposite polarity to that used for collection, between an electrode beneath the deposition surface (FIG. 1.8, FIG. 3.8, and FIG. 1.20) and another electrode (FIG. 2.21), which may be a plate or ring beneath an air filter (FIGS. 1.18 and 3.18), may result in a strong repulsive force being exerted on to the acquired airborne particulate matter located on the deposition surface (FIG. 1.8, FIG. 3.8, and FIG. 1.20). Air flow may additionally be concentrated on the cleaning area (FIG. 3.22) generating an additional force due to a relative difference of atmospheric pressure on the acquired airborne particulate matter located on the deposition surface (FIG. 1.8, FIG. 3.8, and FIG. 1.20) and creating an additional cleaning effect. Furthermore, a charged or uncharged piece of foam, brush, sponge, stopper, or other physical object (FIG. 3.23) may be used to generate a physical force on the acquired airborne particulate matter located on the deposition surface (FIG. 1.8, FIG. 3.8, and FIG. 1.20) and mechanically remove persistent acquired airborne particulate matter located on the deposition surface (FIG. 1.8, FIG. 3.8, and FIG. 1.20). In an embodiment of the disclosure, the deposition surface cleaning area (FIG. 3.22) may be oriented in such a way that a gravitational force acts on the acquired airborne particulate matter located on the deposition surface (FIG. 1.8, FIG. 3.8, and FIG. 1.20), encouraging the acquired airborne particulate matter to drop away from the deposition surface (FIG. 1.8, FIG. 3.8, and FIG. 1.20) within the deposition surface cleaning area (FIG. 3.22) and may be in combination with the exertion of an electrostatic force, a force created from the relative difference of atmospheric pressure, and physical force. In an embodiment of this disclosure, the electrostatic, difference in atmospheric pressure, physical, and gravitational forces represent separate removal mechanisms and may all be present individually or in combination within a concentrated area (FIG. 3.22) to give maximal cleaning and avoid contaminating of the deposition surface (FIG. 1.8, FIG. 3.8, and FIG. 1.20) during sampling collection cycles.

The analysis method of this disclosure (FIG. 6) enables the determination of the identity of acquired airborne particulate matter. The images acquired by an embodiment of this disclosure may be processed partially or completely by the computer processor within the disclosure or may be transmitted to off-site servers for partial or complete processing. Image processing may comprise three dimensional (3D) reconstruction from lighting, image compositing, correction, or other processing to enhance image quality including, but not limited to, histogram equalization, sharpness enhancement, and edge detection. Images may be analyzed manually by a human, via automated counting algorithms, or both. After analysis, the images may be kept in a storage repository for later analysis, or may be discarded. In an embodiment of this disclosure, the device may send raw imagery to a cloud service wirelessly or over a network cable (FIG. 1.19), but may also run a neural network-based algorithm (described below) trained to recognize various identities of acquired airborne particulate matter including species, genera, or family of pollen grains; species, genera, or family of fungal spores; species, genera, or family of bacterial cells; species of internal engine combustion by-products; or the identity of other airborne particulate matter.

An embodiment of this disclosure may identify acquired airborne particulate matter in the captured digital images by using image segmentation algorithms, known informally as "blobbing" techniques. Maximally Stable Extremal Regions (MSER) 1131 and other algorithms produce a series of regions pertaining to each identified feature. Each identified acquired airborne particulate matter feature may be known as a segment. For segments larger than a configured threshold, the segment's image may be passed into a proximal classifier function which may determine whether the segment is most likely to be a) a single simple object; b) a single compound object; or c) a cluster of objects. If the segment appears to be a cluster, a declustering function utilizing concavity and seam based splitting may iteratively break overlapping segments into a series of masked out sub-segments. The classifier function thus described may be necessary to identify certain airborne particulate matter such as pollen which may have compound features, resulting in concavities.

For each segment (acquired airborne particulate matter features identified by the MSER or similar algorithm), or group of segments if there are multiple acquired airborne particulate matter features located at the same optimal focus location, an embodiment's software may step to said focus position and engage the lighting and imaging system described above. The lighting and capture system involves sequentially turning on LED lights (FIGS. 1.12, 2.12, 3.12 and 4.12) and capturing images lighted under various illumination intensities and from various illumination perspectives. ROB LED lights may be strategically placed on a reflective surface (FIGS. 1.12, 2.12, 3.12 and 4.12) around the perimeter of the objective lens (FIG. 1.13 and FIG. 2.13) and may be individually controlled to illuminate the acquired airborne particulate matter from a multitude of perspectives, light intensity levels, and wavelengths. Acquired airborne particulate matter may be sequentially imaged with oblique lighting from multiple vantage points, highlighting the features, topology, transparency, and absorption at light wavelengths from 200 to 800 nanometers.

In an embodiment of the disclosure, multiple obliquely lit image segments may be used to infer three dimensional (3D) shape characteristics and surface features of the acquired airborne particulate matter. Light transmissibility and reflectivity may also be inferred using this multiple lighting angle approach. To infer 3D features, a software model may be constructed starting with a malleable primitive object, a sphere may be used as a reasonable malleable primitive object. The model may be scaled to match the maximal extent of the aggregate captured image and may then be sculpted inward based on the perimeter shape. Highlights from each directionally lit image may be then used to push or pull portions of the model according to the 3D vector of the particular light. If the object's facing surface is determined to be convex, highlights that appear on the side opposite the light may be treated as being on the far end of the translucent object, thus shaping may be possible on both the facing and opposing sides. Once a 3D representation of the object is constructed, its position may be normalized, a color or texture is applied to it based on the captured image(s) of the acquired airborne particulate matter, and may be rendered with high-contrast lighting. The resulting rendering may be composed with the original image, or may be used for direct observation. Alternatively, the 3D representation may serve as input to a classifier that is suitable for working with 3D models.

An embodiment of this disclosure may implement machine vision to recognize and classify acquired airborne particulate matter via a neural network classifier. Prior to classification, various image pre-processing commonly used in machine vision may be applied, comprising histogram equalization, sharpness enhancement, and edge detection. Neural networks may be generally defined by a set of interconnected input "neurons". The connections may have numeric weights that can be tuned based on experience, making the neural network adaptive to inputs and thus capable of learning. The characterization algorithms may activate and weight neurons by the pixel values of an individual input image. After initial weighting, the values may be passed to other neurons where they may be transformed by other functions relative to a library of identification criteria and then may be passed on again to other neurons. This process may be iterative and may repeat until the output neuron is activated and classification probabilities are achieved. The resulting probabilities may be further weighed and identification may be achieved using a statistical model of spatial and temporal abundance of the airborne particulate matter, so that a particular acquired airborne particulate matter such as a pollen grain that may be deemed by the classifier to be equally likely to be either of two genera, will be weighted towards the genera that is most likely for that location and time of year.

Segment images and associated analysis data may be, in an embodiment of this disclosure, available online to those authorized to access them. In addition to displaying the images, a human operator may be able to give feedback regarding classification, which feedback and corrections may be used to improve the training of the classifier. The series of segmentation images, comprising the digital imagery or particle topology inputs as well as initial particle determinations, may be used directly or with further processing as inputs to classification software or may be analyzed by a human, either remotely or locally, to produce airborne particulate matter identity determinations. The statistical, spatial and temporal model may also be improved, using data coming from devices, as well as correctional feedback from software users.

In an embodiment of the disclosure, captured images may be processed by the onboard computer (FIG. 1.15), and the resulting images and data may be stored until internet communication is established with a remote network storage system via a cable (FIG. 1.19) or Wi-Fi connection integrated with the onboard computer (FIG. 1.15). The computer processor within the disclosure (FIG. 1.15) or off-site cloud servers may make the captured images and count results available online and via push notification. Quantification of the acquired airborne particulate matter based on the time each portion of the deposition surface (FIG. 1.8, FIG. 3.8, and FIG. 1.20) was actively sampled and collected may be accomplished and included with the results.

The disclosure has been described in an illustrative manner, and it is to be understood that the terminology which has been used is intended to be in the nature of words of description rather than of limitation. Obviously, many modifications and variations of the present disclosure are possible in light of the above teachings. For example, the device could include mechanisms to direct air currents strategically or to protect itself from adverse environmental and weather conditions. Embodiments may use various deposition media on which to collect particulates, various methods for positioning the particulates for imaging, and various methods of lighting and imaging specimens. Embodiments may also implement practical variants by allowing users flexibility in the kinds of enclosures and mounting mechanisms.

REFERENCES

1. Akinbami, L., *Asthma prevalence, health care use and mortality, 2003-05. Guide for State Health Agencies in the Development of Asthma Programs; US Department of Health and Human Services, Centers for Disease Control and Prevention. CDC.* Available at: www.cdc.r;ovlnchs/products/pubs/pubdlhestats/asthma/asthma.htm. 2006
2. Barnett, S. B. L. and T. A. Nurmagambetov, *Costs of asthma in the United States:* 2002-2007. Journal of Allergy and Clinical Immunology, 2011. 127(1): p. 145-152.
3. Lucas, R. W., J. Dees, R. Reynolds, B. Rhodes, and R. W. Hendershot, *Cloud-computing and smartphones: Tools for improving asthma management and understanding environmental triggers.* Annals of Allergy, Asthma & Immunology, 2015. 114: p. 431-432.
4. Eder, W., M. J. Ege, and E. von Mutius, *Current concepts: The asthma epidemic.* New England Journal of Medicine, 2006. 355(21): p. 2226-2235.
5. Beggs, P. J., C. H. Katelaris, D. Medek, F. H. Johnston, P. K. Burton, B. Campbell, A. K. Jaggard, D. Vicendese, D. Bowman, I. Godwin, A. R. Huete, B. Erbas, B. J. Green, R. M. Newnham, E. Newbigin, S. G. Haberle, and J. M. Davies, *Differences in grass pollen allergen exposure across Australia.* Australian and New Zealand Journal of Public Health, 2015. 39(1): p. 51-55.
6. Anderson, H. R., G. Favarato, and R. W. Atkinson, *Long-term exposure to outdoor air pollution and the prevalence of asthma: meta-analysis of multi-community prevalence studies.* Air Quality Atmosphere and Health, 2013. 6(1): p. 57-68.
7. Brook, R. D., S. Cakmak, M. C. Turner, J. R. Brook, D. L. Crouse, P. A. Peters, A. van Donkelaar, P. J. Villeneuve, O. Brion, M. Jerrett, R. V. Martin, S. Rajagopalan, M. S. Goldberg, C. A. Pope, and R. T. Burnett, *Long-Term Fine Particulate Matter Exposure and Mortality From Diabetes in Canada.* Diabetes Care, 2013. 36(10): p. 3313-3320.
8. Zhang, Y., L. Bielory, Z. Y. Mi, T. Cai, A. Roback, and P. Georgopoulos, *Allergenic pollen season variations in the past two decades under changing climate in the United States.* Global Change Biology, 2015. 21(4): p. 1581-1589.
9. Moorman, J., L. Akinbami, C. Bailey, and et al., *National Surveillance of Asthma: United States, 2001-2010. National Center for Health Statistics.* Vital Health Stat, 2012. 3(35).
10. Zhang, Y., L. Bielory, T. Cai, Z. Mi, and P. Georgopoulos, *Predicting onset and duration of airborne allergenic pollen season in the United States.* Atmospheric Environment, 2015. 103: p. 297-306.
11. Eggen, B., S. Vardoulakis, D. Hemming, and Y. Clewlow. *Pollen forecasting, climate change & public health.* in *Int. Conj on Climate Change Effects.* 2013.
12. Myszkowska, D. and R. Majewska, *Pollen grains as allergenic environmental factors-new approach to the forecasting of the pollen concentration during the season.* Annals of agricultural and environmental medicine: AAEM, 2014. 21(4): p. 681-688.
13. Wassenberg, J., Bulatov, D., Middelmann, W., Sanders, P.: Determination of Maximally Stable Extremal Regions in Large Images. In: Signal Processing, Pattern Recognition, and Applications. (February 2008).

What is claimed is:

1. An apparatus to illuminate and capture images of airborne particulate matter collected on a deposition surface comprised of:
   a. multiple controlled light sources situated in a ring surrounding the airborne particulate matter and emitting ultraviolet, visible, and/or near infrared electromagnetic light at a high angle of incidence to the top surface of the airborne particulate matter;

b. an imaging unit oriented to observe the airborne particulate matter and situated adaxial to the light sources;

c. a control unit for the light sources and the imaging unit which individually modulates the light sources and activates the imaging unit so as to capture a series of images of the airborne particulate matter illuminated from different adaxial directions, over a range of the electromagnetic frequencies, and across a range of illumination intensities.

2. The apparatus according to claim 1, whereby knowledge of the direction, frequency, and intensity of the light source is used by software to infer the topology of the airborne particulate matter.

3. The apparatus according to claim 1, whereby the series of images are used directly or with further processing as inputs to classification software or are analyzed by a human to produce airborne particulate matter identity determinations.

4. The system according to claim 3, whereby particle identification is achieved by weighing initial said particle type determinations against a statistical model derived from a database of spatial and temporal abundance of the airborne particulate matter.

* * * * *